United States Patent [19]
Hiss, III et al.

[11] Patent Number: 5,970,781
[45] Date of Patent: Oct. 26, 1999

[54] IN-STACK DIRECT PARTICULATE MASS MEASUREMENT APPARATUS AND METHOD

[75] Inventors: John Hiss, III, Castleton; Harvey Patashnick, Voorheesville, both of N.Y.

[73] Assignee: Rupprecht & Patashnick Company, Inc., Albany, N.Y.

[21] Appl. No.: 09/078,909

[22] Filed: May 14, 1998

[51] Int. Cl.⁶ .......................... G01N 15/06; G01N 37/00
[52] U.S. Cl. ................... 73/28.01; 73/24.03; 73/863.82; 73/863.52
[58] Field of Search ............................ 73/28.01, 863.22, 73/863.82, 863.55, 24.03, 28.05, 23.33, 863.52

[56] References Cited

U.S. PATENT DOCUMENTS

| | | | |
|---|---|---|---|
| 3,005,347 | 10/1961 | Smithson | 73/423 |
| 3,068,694 | 12/1962 | Worswick | 73/194 |
| 3,633,405 | 1/1972 | Noll | 73/28 |
| 3,707,869 | 1/1973 | Raynor | 73/28 |
| 3,926,271 | 12/1975 | Patashnick | 177/210 |
| 4,114,557 | 9/1978 | De Brey | 116/67 R |
| 4,189,937 | 2/1980 | Nelson | 73/28 |
| 4,391,338 | 7/1983 | Patashnick | 177/210 |
| 4,660,408 | 4/1987 | Lewis | 73/28 |
| 4,815,314 | 3/1989 | Plank | 73/28 |
| 5,006,227 | 4/1991 | Behm et al. | 209/143 |
| 5,090,233 | 2/1992 | Kogure et al. | 73/28.05 |
| 5,369,981 | 12/1994 | Merz et al. | 73/28.01 |
| 5,571,946 | 11/1996 | Koshi et al. | 73/28.01 |
| 5,665,902 | 9/1997 | Wang et al. | 73/28.01 |
| 5,739,413 | 4/1998 | Kohn et al. | 73/23.31 |

FOREIGN PATENT DOCUMENTS 4-191639  7/1992  Japan.

*Primary Examiner*—Hezron Williams
*Assistant Examiner*—J. David Wiggins
*Attorney, Agent, or Firm*—Heslin & Rothenberg, P.C.

[57] ABSTRACT

The mass of particulate of an effluent gas flowing in a stack is directly measured with a mass measurement assembly supported within the stack. The mass measurement assembly preferably includes an inertial mass measurement transducer which provides near real-time mass readings. The mass measurement assembly also includes a particulate collector which can be equilibrated in situ. A conditioned gas line supplies clean, dry, heated conditioned gas to the collector for equilibration. The flow rate of the conditioned gas prevents effluent gas from reaching the collector during equilibration. The collector can be equilibrated in the stack before and after sampling and between intermittent sampling periods.

35 Claims, 4 Drawing Sheets

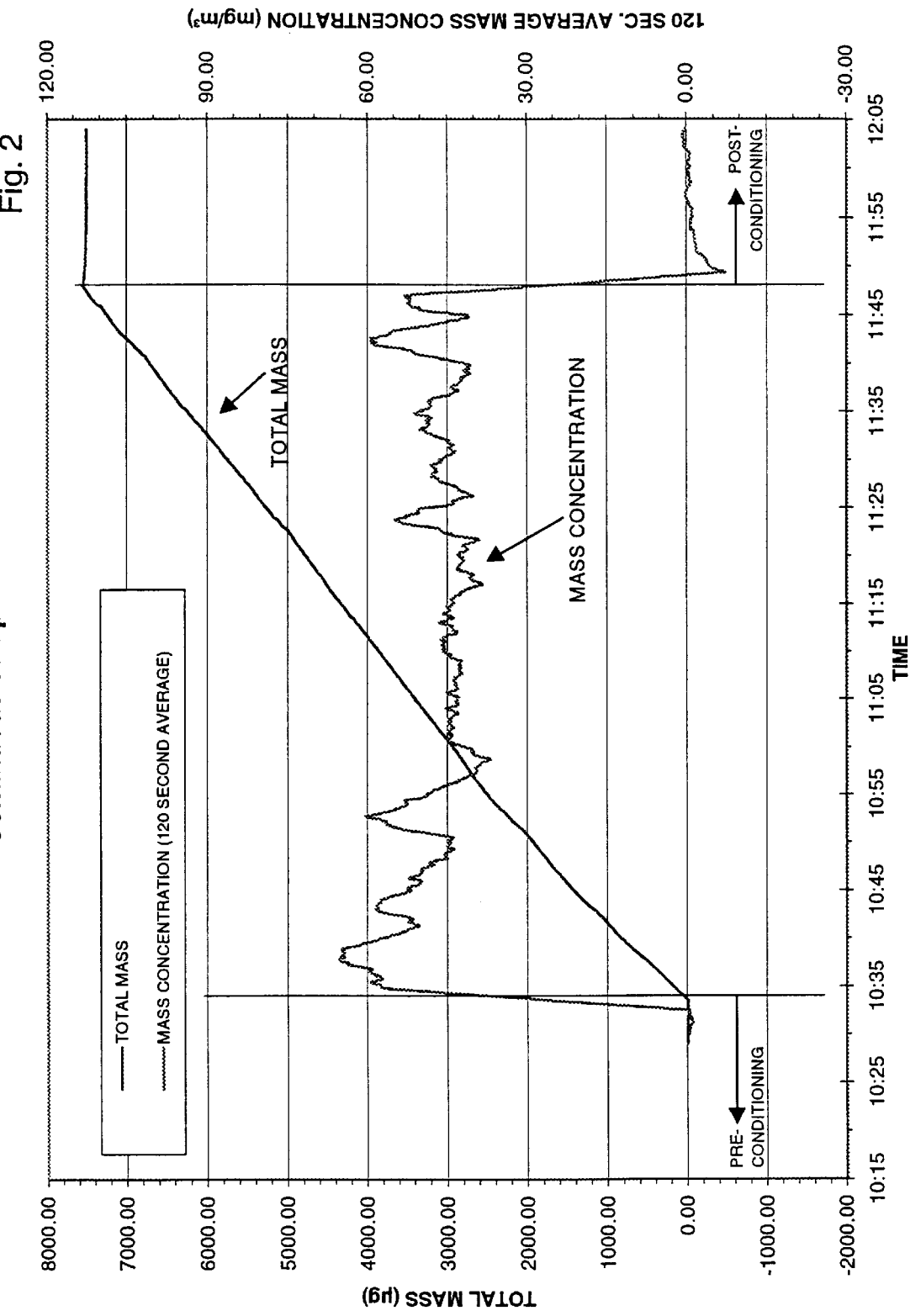

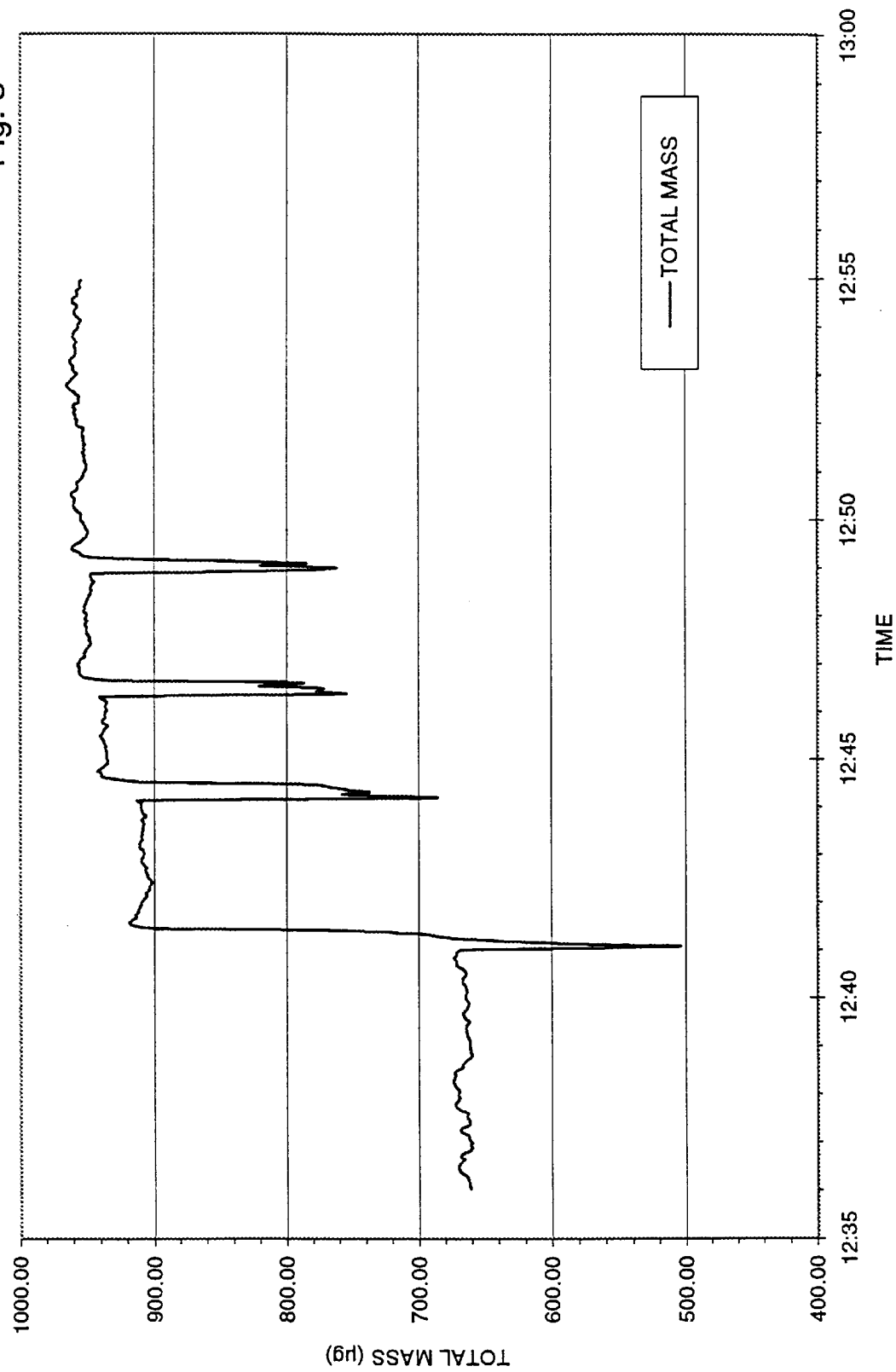

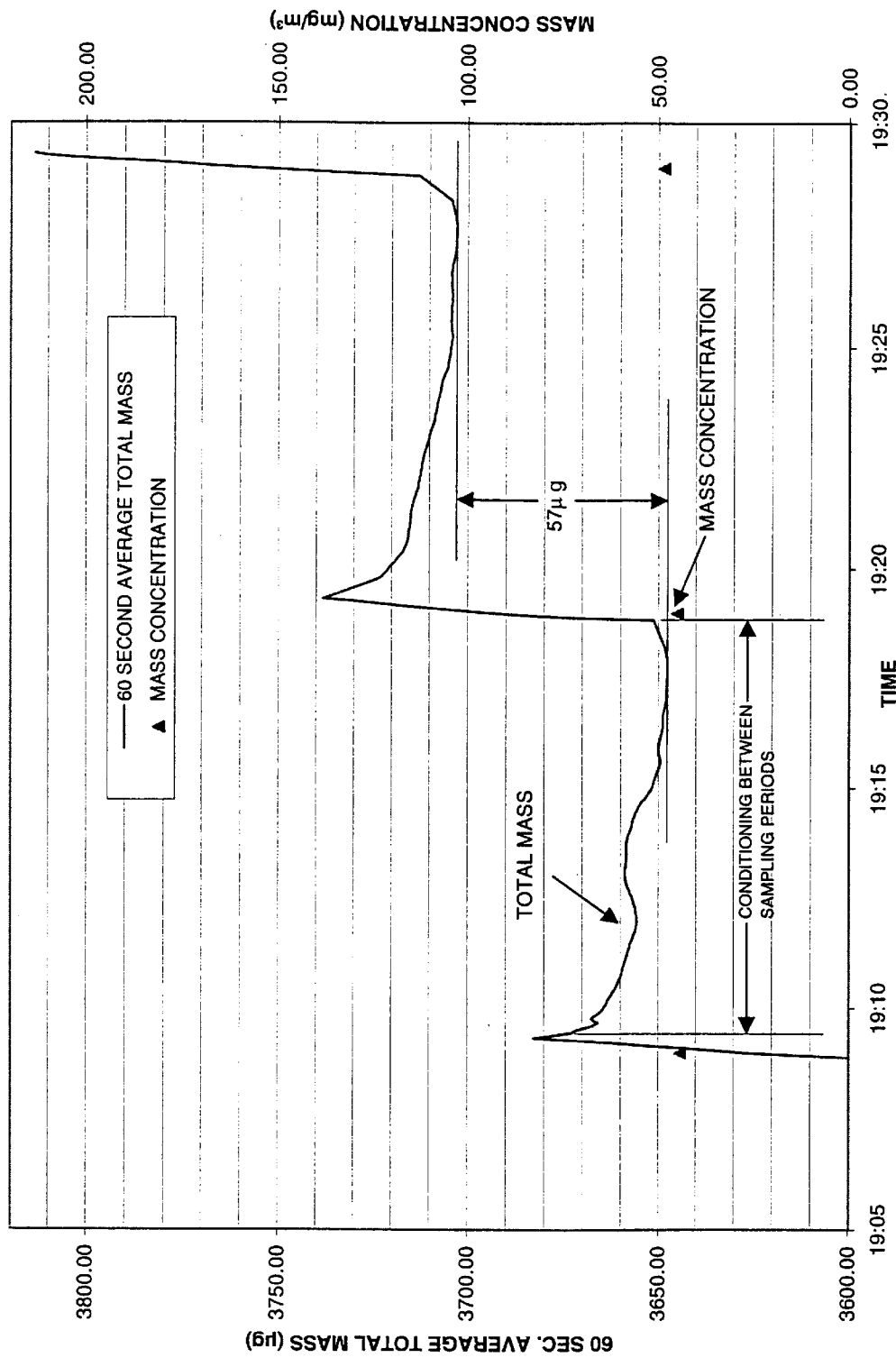

IN-STACK DIRECT PARTICULATE MASS MEASUREMENT APPARATUS AND METHOD

RELATED APPLICATION

This application is related to commonly assigned application Ser. No. 09/014,252, filed on Jan. 27, 1998, and incorporated herein by reference in its entirety.

FIELD OF THE INVENTION

This invention relates generally to particulate matter mass measurement instruments, and more particularly to such instruments used to collect and measure particulate matter of effluent gas flowing in a stack or other exhaust conduit of a stationary source.

BACKGROUND ART

The measurement of particulate matter of effluent gas flowing in a stack or other exhaust conduit of such stationary sources as coal burning facilities, garbage incinerators, hazardous waste type incinerators, concrete plants, paper/pulp processing plants and the like, is important because of the relationship between particulate matter and adverse health effects. Particulate matter exiting a stack of such an industrial source disburses into the atmosphere where it is inhaled by humans. Suspended particulate matter is known to produce a variety of deleterious health effects when inhaled. Monitoring of the particulate mass and/or concentration of the effluent gas in a stack is, therefore, important for health reasons.

Particulate matter exiting a stack is made up of many regulated substances. Measurement of particulate matter mass can also be used as a surrogate measurement of these other regulated substances.

Accordingly, regulatory agencies around the world require the continuous measurement of particulate matter emissions from stacks. A disadvantage of all present continuous stack particulate monitors—opacity, triboelectric, acoustical, and beta attenuation—is that they do not directly weigh particulate and must be periodically calibrated using manual mass measurements.

Manual measurement methods are defined in terms of utilizing a filter medium to capture particulate matter while measuring the total volume of effluent gas which has been filtered at the stack temperature by the medium over a period of time. There are various approaches available to unambiguously determine the flow rate through the filter over time and, hence the volume of gas sampled. However, effluent gas often contains water which adds non-particulate mass to the filter medium. To accurately represent the filter mass, the uncombined water must be removed.

As a result, the current Environmental Protection Agency (EPA) reference method (Method 17) in the United States is a manual method that requires the removal of uncombined water prior to and following particulate collection. The manual method consists of: (1) filter equilibration under a predefined range of temperature and humidity conditions; (2) a pre-collection weighing of the filter; (3) the installation of the filter in the manual sampler and the obtaining of a representative effluent gas sample from within the stack; (4) the removal of the filter from the stack and the sampler, and post-collection clean up of the nozzle and housing (all particulate on the walls of the nozzle and filter housing leading to the filter medium must be collected as part of the sample); (5) post-collection conditioning under the same equilibrium conditions for the filter as performed in the preconditioning (this procedure removes uncombined water from the sample and filter medium); and finally, (6) post-collection weighing of the filter to determine the mass captured on the filter medium. Steps (1), (2), (5) and (6) are normally implemented in the controlled environment of a laboratory remote from the stack. Because of the filter and apparatus handling required, this manual measurement method contains many opportunities for measurement error. It is also very labor intensive, tedious and expensive. The method provides only an average particulate concentration for the sample period, and requires a great deal of care to give repeatable results because of the many inherent sources of error such as filter handling, transport, conditioning and weighing. Another disadvantage is that useful time history information, describing transients and stack stratification, is lost. An easier, faster, more repeatable technique would also allow for more accurate and frequent calibrations of the present indirect continuous emission monitors.

A need thus persists for a particulate mass measurement instrument which reduces many of the error sources associated with manual sampling, and provides more representative data, easier, faster and with enhanced accuracy.

SUMMARY OF THE INVENTION

This need is satisfied, shortcomings of the existing art are overcome, and additional benefits are realized, in accordance with the principles of the present invention, through the provision of an in-stack mass measurement instrument which accurately measures mass of particulate of effluent gas directly and in near real-time. Further, in-stack equilibration of the particulate collector eliminates the need for pre- and post-sampling laboratory work.

In accordance with a first aspect of the present invention, apparatus for directly measuring mass of particulate of effluent gas flowing in a stack includes an inertial mass measurement assembly. This assembly includes a mass transducer, a particulate collector connected to the mass transducer, and an inlet tube for directing sampled gas towards the collector. A support structure supports the mass measurement assembly within the stack with the inlet tube oriented for sampling effluent gas flowing in the stack. Accordingly, sampled effluent gas enters the tube and is directed toward the collector. A conditioned gas supply line selectively supplies conditioned gas to the collector while the mass measurement assembly is supported within the stack. The conditioned gas can be advantageously employed to equilibrate, condition and/or purge the collector prior to sampling, after sampling, and/or between sampling periods.

A temperature controller can be associated with the supply line for controlling temperature of the conditioned gas. The temperature controller can be employed to supply the conditioned gas to the particulate collector at substantially the same temperature as sampled effluent gas or at another set temperature. In one embodiment, the temperature controller comprises a heat exchanger for maintaining the conditioned gas at substantially the same temperature as the sampled effluent gas. A section of the supply line upstream of the heat exchanger can be heated to preheat conditioned gas entering the heat exchanger.

The conditioned gas preferably comprises a desiccated, clean, preheated gas. In addition to conditioning the collector, the conditioned gas can be used to prevent effluent gas from reaching the collector and/or to selectively dilute sampled effluent gas. The conditioned gas supply line preferably includes a pump, a flow controller, a filter, a gas dryer, a switching valve and a heat exchanger.

According to a further aspect of the present invention, a controller of the particulate mass measuring apparatus mandates supply of the conditioned gas to the collector prior to a sampling period to precondition the collector and after the sampling period to postcondition the collector and collected particulate. For intermittent sampling of the effluent gas, the controller can mandate supply of the conditioned gas to the collector between sampling periods.

The mass transducer located within the stack can preferably comprise a hollow elastic element vibrating in a clamp-free mode. The particulate collector preferably comprises a filter mounted on a free end of this elastic element.

According to another aspect of the present invention, an indicator or other output device connected to the mass transducer provides an indication of total mass and/or mass concentration of collected particulate, with uncombined water substantially reduced.

The support structure of the particulate mass measuring apparatus of the present invention can include an extendible boom inserted into the stack and supporting the mass measurement assembly at a remote end thereof. The mass measurement assembly can be rotationally mounted to the boom. A preferred boom mounting arrangement allows the mass measurement assembly to traverse the stack to sample effluent gas at different locations within the stack.

A sampling line conveys gas from the vicinity of the collector to outside the stack. The sampling line preferably includes a condenser, a heated section upstream of the condenser, and a reduced pressure pump downstream of the condenser.

In accordance with still another aspect of the present invention, an improved in-stack mass determining device which determines mass of material in an effluent gas flowing in a stack includes an inertial mass measurement transducer and in situ equilibrator located within the stack. The in-stack transducer is connected to a material collector for sampling effluent gas and measuring mass of collected material directly and in near real-time.

The in-stack equilibrator of this improved mass determining device can equilibrate the collector in the stack prior to sampling and equilibrate the collector and the collected material in the stack after sampling. The in-stack equilibrator preferably comprises a supply line for selectively supplying conditioned gas to the collector within the stack. The conditioned gas may comprise desiccated, clean gas with a temperature substantially equal to a temperature of the sampled effluent gas.

According to a further aspect, an in-situ equilibrator for equilibrating a material collector within a stack is included in a mass measurement system. The in-situ equilibrator can comprise a supply line for selectively supplying conditioned gas to the collector within the stack to equilibrate the collector in situ. The conditioned gas can comprise desiccated, clean gas supplied at a set temperature and in a manner which prevents effluent gas from reaching the collector.

The mass measurement assembly of the present invention preferably uses a short, straight inlet tube to isokinetically sample the effluent gas and transport sampled effluent gas to the particulate collector. Following sampling and in-situ postconditioning, the mass measurement assembly can be removed from the stack, stabilized and with flow through the system, the inlet tube can be brushed down. All particulate matter collected on the inlet wall is thereby loosened and collected and immediately weighed for addition to the mass measurement provided during in-stack sampling. Inlet losses are thus reclaimed and weighed on site using the same inertial mass measurement instrument.

The present invention also contemplates a method for measuring mass of material in an effluent gas flowing in a stack. This method includes: locating a material collector within the stack; equilibrating the collector within the stack to provide a preconditioned collector; sampling the effluent gas flowing in the stack; collecting material from sampled effluent gas on the pre-conditioned collector within the stack; equilibrating the collector and collected material within the stack to provide a post-conditioned collector and collected material; and measuring a mass change of said post-conditioned collector and collected material relative to said pre-conditioned collector. Equilibrating preferably involves directing dry, clean, heated gas towards the collector, while measuring preferably comprises determining the mass increase with an inertial mass measurement instrument. The method may also include: directing the sampled effluent gas to the preconditioned collector with an inlet tube; after sampling, brushing down an interior of the inlet tube to collect any additional material which may have lodged on the interior; and measuring the mass of said additional material with the same inertial mass measurement instrument.

The mass measurement instrument and methodology of the present invention directly measures particulate mass concentrations of effluent gas in a stack in near real-time. This instrument may be used to perform EPA Method 17 equivalent test, as well as short-term continuous sampling. In addition, because it resolves mass on line in near real-time, the apparatus of the present invention provides useful plant process information such as transient particulate mass concentrations during ramped loadings, stratification in stacks and control device efficiencies. Another valuable use for the instrument of the present invention is to calibrate existing continuous emission monitors such as opacity, triboelectric, acoustical and beta attenuation monitors that, unlike the present invention, do not possess a direct relationship with particulate mass. The present invention further eliminates the need to transport the sample to a lab for conditioning and weighing. The operation of the instrument of the present invention thus reduces testing errors and provides an accurate and repeatable test protocol.

Many of these advantages can also be realized in applications other than stack monitors, by including an in-situ equilibrator within a mass measurement device for equilibrating a particulate collector within the device. The in-situ equilibrator can precondition and/or postcondition the collector, and can equilibrate the collector alone or the collector and collected particulate.

BRIEF DESCRIPTION OF DRAWINGS

These and other aspects, features and advantages of the invention will become more readily apparent upon reference to the following detailed description of preferred embodiments when read in conjunction with the accompanying drawings, in which:

FIG. 2 is a graphical representation of total mass and mass concentration readings from an in-stack particulate mass measurement instrument of the present invention during in-situ preconditioning, continuous sampling, and in-situ postconditioning time periods;

FIG. 3 is a graphical representation of total mass readings provided by an instrument like that illustrated in FIG. 1 during several brush downs of the interior of an inlet tube of the instrument; and FIG. 4 provides a graphical representation of in-stack conditioning between intermittent sampling periods.

DETAILED DESCRIPTION

Figure 1:
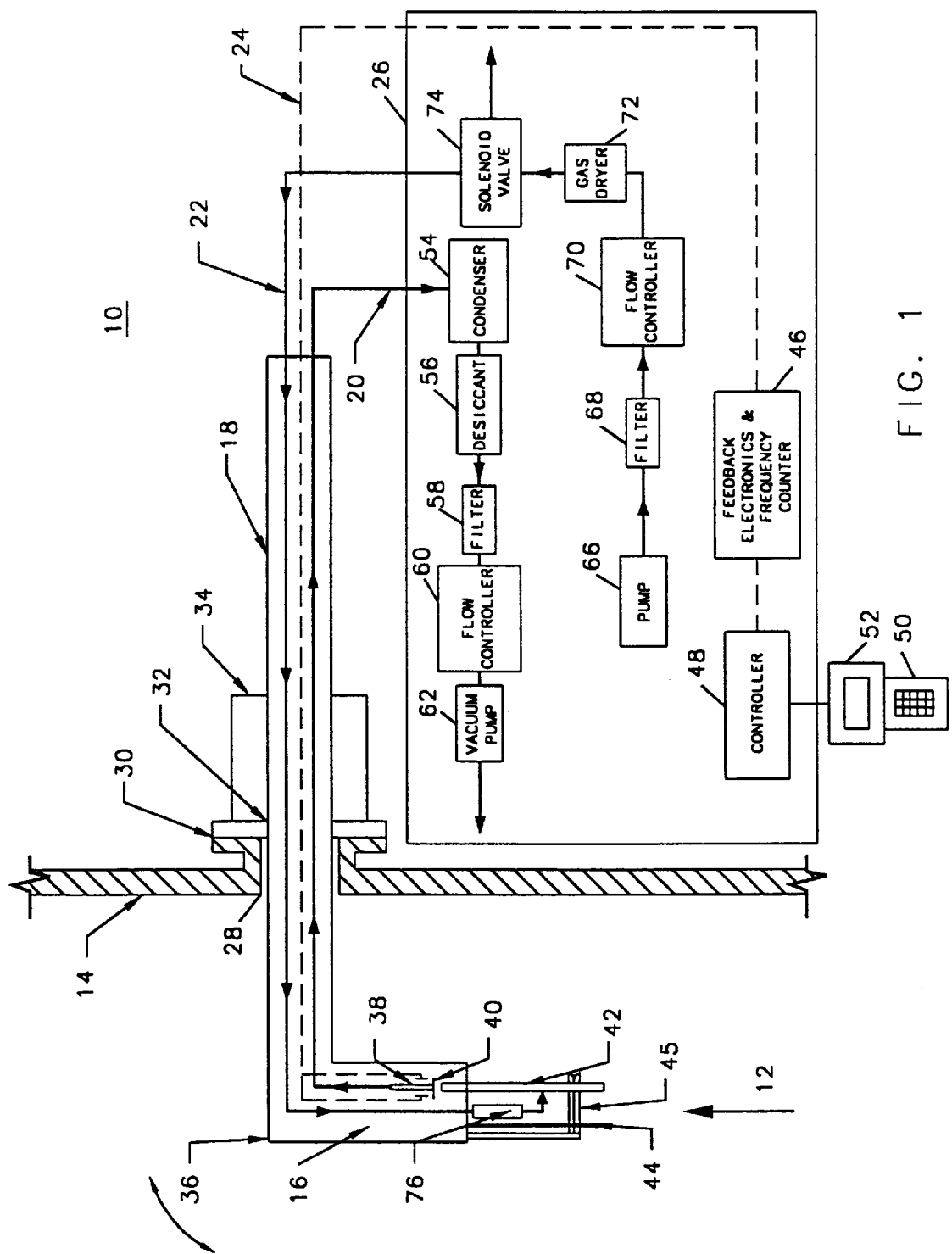
FIG. 1 is a schematic representation of an embodiment of the particulate mass measurement apparatus of the present invention as it can be employed to determine the mass of particulate of effluent gas flowing within a stack.

A particulate mass measurement instrument 10 for measuring the mass of particulate in an effluent gas 12 flowing within a stack 14 in accordance with the principles of the present invention, is illustrated in FIG. 1. This instrument directly measures particulate mass on-line in near real-time with provision for in-stack conditioning of the particulate collector, as more fully described hereinafter.

Mass measurement instrument 10 includes a mass measurement assembly or probe 16 supported within stack 14 at the end of an extendible boom 18, or other support structure. The mass measurement assembly 16 is connected via pneumatic lines 20, 22 and electrical signal line 24 to a control unit 26. The pneumatic and electrical signal lines preferably extend along and through boom 18. Advantageously, pneumatic lines 20 and 22 can be controllably heated, in whole or part, as more fully described hereinafter. Control unit 26 may be located proximate boom 18 or remote therefrom.

Mass measurement instrument 10 is intended for use in measuring the mass of particulate in an effluent gas 12 flowing in a stack 14. The term "stack" is broadly used herein to connote any passageway that has particulate laden gas flowing through it. The term "effluent gas" is used herein to denote any such particulate laden gas. The invention is applicable to any facility which emits particulate laden gas. Such facilities are sometimes referred to in this industry as "stationary sources" and include, but are not limited to: coal burning facilities, garbage incinerators, hazardous waste type incinerators, cement plants, paper/pulp processing facilities, boiler exhaust, and smoke stacks.

As shown in FIG. 1, the wall of stack 14 might typically include a port 28 defined by an exterior flange 30. According to one embodiment of the present invention, a sliding joint 32 and bearing housing 34 are mounted to an outside surface of flange 30. Port 28, sliding joint 32 and bearing housing 34 define an interior passageway through which measurement assembly 16 and boom 18 can be inserted into stack 14. Assembly 16 and boom 18 have an outer diameter slightly smaller than that of port 28. Assembly 16 is mounted to the end of boom 18 by a rotating joint or pivot 36. This joint allows assembly 16 to be oriented coaxially with boom 18 for access into stack 14 through port 28. Following insertion, mass measurement assembly 16 is rotated about joint 36 to an orientation, as shown in FIG. 1, which facilitates sampling of effluent gas 12. After sampling is completed, assembly 16 can be rotated back to its coaxial orientation with boom 18 for ready withdrawal from stack 14 through port 28. Various conventional mechanisms can be used to provide the rotational support and movement to assembly 16, as will be appreciated by those skilled in this art.

While port 28 provides access to the interior of stack 14, sliding joint 32 and bearing housing 34 allow the boom 18 and attached mass measurement assembly 16 to be displaced in order to traverse the interior of the stack, as may be required or desired under various measurement protocols. A quick release clamp (not shown) may be used to temporarily lock slidable boom 18 in place when measurement assembly 16 is positioned at a desired crosswise location within stack 14. Boom 18 is preferably extendible to a maximum desired traverse length, and collapsible to adapt to various field conditions and for ease of transport.

Mass measurement assembly 16 includes a mass transducer 38 connected to a mass collector 40, and an inlet tube 42 for directing sampled effluent gas 12 towards particulate collector 40. Although the components of mass measurement assembly 16 may take many different forms, mass transducer 38 is preferably an inertial mass measurement transducer which provides a direct, near real-time measure of the mass of particulate collected on collector 40. Transducer 38 can advantageously take the form of a hollow elastic element oscillating in a clamp-free mode, as more fully described hereinafter. Collector 40 preferably comprises a filter mounted to transducer 38. An impaction plate or other particulate matter collector can also be used to collect particulate from the sampled effluent gas. Inlet tube 42 is preferably short and straight to minimize inlet losses.

Mass measurement assembly 16 can be used to measure total particulate mass levels, or in conjunction with a cyclone or other device (not shown) that separates particles based on aerodynamic diameter, located upstream of inlet tube 42, to measure $PM_{10}$ or $PM_{2.5}$ particulate mass levels as is well known in the art. Similarly, assembly 16 can be outfitted with a temperature sensor 44 and a pressure sensor 45, e.g. pitot tubes, to facilitate and maintain isokinetic sampling at the entrance of inlet tube 42 as is well known in the art and specifically taught by EPA Method 17—Determination of Particulate Emissions From Stationary Sources (In-Stack Filtration Method), pages 17-1 to 17-8, Rev. 1, dated August 1985 (which document is incorporated by reference herein in its entirety). Although presently preferred, isokinetic sampling may not be necessary when measuring small particulate.

Particulate collector 40 is preferably located near the exit of inlet tube 42 in order to minimize transport losses and ensure integrity of the sample. Collector 40 preferably comprises an exchangeable filter cartridge mounted on the free end of the preferred transducer—a hollow elastic element which is made to oscillate in a clamp-free mode. Construction and operation of an inertial mass measurement instrument employing such an oscillating hollow elastic element is described in detail in commonly assigned U.S. Pat. Nos. 3,926,271 and 4,391,338, and in a Japanese patent publication JP2-324364 (which patents and Japanese patent publication are incorporated herein in their entirety) and is briefly described hereinafter.

The mass transducer 38 is preferably a hollow tube, clamped at one end and free to vibrate at the other. An exchangeable filter cartridge is placed over the tip of the free end. This cantilevered elastic element vibrates at precisely its natural frequency. An electronic control circuit 46 senses its vibration and, through positive feedback, adds sufficient energy to the system to overcome losses. An automatic control circuit (not shown) maintains the vibration during measurement. A precise electronic counter 46 measures the frequency, which has a direct relationship with mass.

The elastic element is a mechanical oscillator with a high quality factor whose frequency can be described with two parameters, the restoring force constant, K, and the mass, m, consisting of the mass of the filter, $m_f$, the effective mass of the elastic element, $m_0$, and the filter loading $\Delta m$.

$$m = m_f + m_0 + \Delta m \qquad (1)$$

The relationship between these quantities is given by the simple harmonic oscillator equation:

$$4\pi^2 f^2 = K/m \quad (2)$$

or $$f^2 = K_0/m \text{ with } K_0 = K/4\pi^2. \quad (3)$$

Calibration Process

If a known mass, $\Delta m$ (determined gravimetrically) is placed on the filter, $K_0$ can be determined from the frequencies $f_1$ and $f_2$ where $f_1$ is the frequency without $\Delta m$, and $f_2$ is the frequency after loading with $\Delta m$.

$$f_1^2 = K_0/(m_f + m_0) \quad (4)$$

$$f_2^2 = K_0/(m_f + m_0 + \Delta m) \quad (5)$$

From these two equations $K_0$ can be calculated for a particular device:

$$K_0 = \Delta m/(1/f_2^2 - 1/f_1^2) \quad (6)$$

The elastic element is made of nonfatiguing inert material and retains its calibration indefinitely.

Mass Measurements

Once $K_0$ is determined for a particular elastic element, it can be used for mass measurements.

If the element is oscillating at the frequency of $f_a$ and exhibits the frequency $f_b$ after an unknown mass uptake $\Delta m'$, this mass uptake can be obtained as a function of $f_a$, $f_b$ and $K_0$. It is:

$$f_a^2 = K_0/m \quad (7)$$

$$f_b^2 = K_0/(m + \Delta m') \quad (8)$$

where m is the total mass of the system before the mass uptake. Elimination of m yields the fundamental equation for mass uptake.

$$\Delta m' = K_0(1/f_b^2 - 1/f_a^2) \quad (9)$$

Note that the starting frequency, $f_a$, can be defined at any arbitrary time, and a mass measurement does not depend on the knowledge of the previous loading of the filter. Tracking frequency with time yields the mass rate, and when combined with measured flow rate through the filter, produces the mass concentration. Such tracking and calculations can be readily accomplished, in known fashion by a computer/controller or processor 48 in control unit 26. A keypad 50 and display 52, or other input/output devices can be connected to controller 48 to facilitate operator interface therewith and to indicate mass readings provided by instrument 10.

Referring again to FIG. 1, sampling line 20 connects mass transducer 38, e.g. the described hollow elastic element, to a condenser 54 located outside of stack 14. At least a portion of sampling line 20 is preferably heated to prevent moisture condensation therein. Condenser 54 in conjunction with optional desiccant 56 serve to remove moisture and thoroughly dry the sampled gas before it passes through an additional optional filter 58, mass flow controller 60 and is exhausted through reduced pressure (e.g. vacuum) pump 62.

In operation, effluent gas 12 enters inlet tube 42 and passes directly therethrough to collector 40 mounted on the oscillating element or other mass transducer 38. The particulate matter in the sampled effluent gas can be collected by collector 40 at stack temperature as described in EPA Method 17. The sampled gas then proceeds through heated sampling line 20 in boom 18 to condenser 54 and then through the remaining elements of the sampling train. In this manner, direct measurements of the mass of particulate matter deposited on collector 40 can be obtained in near real-time on-site.

EPA Method 17 requires the removal of uncombined water from a collected sample. The present invention provides for in-stack purging of such uncombined water, as well as equilibration of the collector prior to and after sampling. Equilibration comprises establishing a stable, reproducible thermodynamic condition for the collector before and/or after sampling. Collector conditioning between intermittent sampling periods can also be effectuated.

In accordance with this feature of the present invention, a conditioned gas line 22 extends through boom 18 and connects to inlet tube 42 in order to selectively supply conditioned gas to collector 40. The conditioned gas preferably comprises a dry clean gas provided by pump 66 through a filter 68, flow controller 70, gas dryer 72, and solenoid valve 74 to line 22. The components of this conditioned gas train may be conventional, off-the-shelf type elements. Such elements are preferably located in control unit 26 outside of stack 14.

Also associated with conditioned gas line 22 is a heat exchanger 76 or other conditioned gas temperature controller. As shown in FIG. 1, heat exchanger 76 is preferably located within stack 14 to conveniently ensure that the conditioned gas stream is at the effluent gas temperature. The heat exchanger may be either active, passive or a combination of both active and passive. Temperature sensor 44 can be employed for such active control. The heat exchanger may take various known forms. A section of conditioned gas line 22 upstream of heat exchanger 76 can optionally be heated to preheat said gas entering the exchanger.

If desired, heat exchanger 76 or other temperature controller can be used to adjust the temperature of the conditioned gas to any set temperature, e.g. a temperature higher than that of the effluent gas.

Flow controller 70 controls the rate of flow of the conditioned gas while filter 68 and gas dryer 72 serve to ensure that the conditioned gas is clean and dry. Solenoid valve 74 serves to quickly turn on and off the supply of conditioned gas to line 22. When not in use, the conditioned gas is exhausted through solenoid valve 74. The activation and operation of the components of the conditioning gas train, as well as the components of the sampling train can all be controlled by controller 48, in known fashion.

The conditioned gas can advantageously be provided with a flow rate greater than that of the sampled effluent gas so that when collector 40 is to be conditioned, equilibrated and/or purged by the conditioned gas, effluent gas is prevented from reaching the collector, i.e. backflow of the conditioned gas towards the entrance of inlet tube 42 due to its higher flow rate effectively blocks the entry of effluent gas into tube 42.

Alternatively, the flow along sampling line 20 can be controlled to effectively dilute the sampled effluent gas with conditioned gas. This approach might be used to extend collector life or to reduce the amount of moisture reaching the collector in order to enhance the ability of the collector to collect particulate or to decrease any postconditioning time.

When the flow rate of the conditioned gas is such as to prevent effluent gas sampling, the conditioned gas can be employed to equilibrate collector 40 in situ. Such equilibration can be used to precondition the collector prior to sampling and to postcondition the collector and any collected particulate after sampling, yielding results directly comparable to EPA (Environmental Protection Agency)

Method 17, while avoiding the difficulties and delays associated with laboratory equilibration. Such collector conditioning can also be effectuated between intermittent sampling periods thereby extending the available life of the collector.

The conditioned gas line can provide for a constant stable flow rate to and a constant temperature at the collector during conditioning and sampling. In situ conditioning thus does not disturb the state of the collector-mass transducer combination.

The in-stack particulate mass measurement instrument of the present invention may be operated in various modes: continuous measurements at a single point, timed traverse measurements at multiple points, or time proportioned (intermittent) sampling, e.g. for calibration of indirect continuous emission monitors. Continuous uninterrupted sampling is used for relatively short duration tests, on the order of a few hours, similar to an EPA Method 17. Because collector life is a function of the type of particulate matter as well as the concentration, test durations on the order of days may be possible. Collector life can be extended by sampling for only a portion of the time. This "time proportioned sampling" technique lengthens the time between collector changes, and can be used to calibrate present continuous monitors on a regular basis. For example, a scheme where sampling by instrument 10 occurs for a short time each hour and is compared with opacity readings taken by a separate continuous emission monitor during the same period would allow the constant updating of the continuous monitor calibration.

A typical sequence of operation for the particulate mass measurement instrument 10 of the present invention will now be described. Initially the complete instrument is checked for leaks and then a collector 40 is installed in mass measurement assembly 16. Assembly 16 coaxially aligned at the end of boom 18 is then inserted through access port 28 into stack 14 and rotated into its sampling position with conditioned gas line 22 activated. The flow rate of the conditioned gas into inlet tube 42 prevents any effluent gas 12 from reaching collector 40 and permits preconditioning of this collector within the stack. The instrument is allowed to stabilize, i.e. the temperature of the conditioned gas, due to the heat exchanger or other temperature controller, rises to that of the effluent gas. As shown in FIG. 2 this preconditioning establishes a zero baseline for future mass readings.

Once the collector has been preconditioned, sampling can begin by activating solenoid valve 74 to shut off the supply of conditioned gas to collector 40. Sampling line 20 now draws effluent gas in through inlet tube 42 for collection of particulate matter on collector 40. As illustrated in FIG. 2 during sampling, the total mass and/or mass concentration of the effluent gas can be directly determined and indicated in known fashion by the particulate mass measurement instrument.

At the conclusion of sampling, solenoid valve 74 is again activated to supply the conditioned gas to inlet tube 42. The higher flow rate of the conditioned gas again blocks effluent gas from reaching the collector. The dry, clean, heated conditioned gas removes uncombined water and serves to postcondition the collector and collected particulate, as illustrated in FIG. 2.

Following the postconditioning, assembly 16 is withdrawn from stack 14 through access hole 28, the conditioned gas line 22 is deactivated and assembly 16 is preferably temperature stabilized outside the stack, for example with an insulation blanket, to maintain assembly 16 at substantially the stack temperature. With the sampling line 20 still activated, the interior of inlet tube 42 can then be brushed down several times to collect and measure, using the same measurement instrument 10, any particulate matter which may have lodged along the interior walls of the tube during sampling. Mass readings resulting from brush down are illustrated in FIG. 3. The mass reading from brush down can be added to the mass reading obtained during sampling to provide a more accurate indication of the total mass particulate in the effluent gas.

As illustrated in FIG. 4, the conditioned gas may also be advantageously used to condition the collector between time proportioned (i.e. intermittent) sampling periods. The difference in total mass readings between consecutive stabilized conditioning periods provides a measure of the mass increase occurring during the intermediate sampling period.

From the above description, it will be readily apparent to those skilled in this art that an in-stack particulate mass measurement instrument has been provided which overcomes many of the disadvantages of the prior art and provides additional benefits. The need for pre- and postconditioning and weighing of a particulate collector in a laboratory is eliminated as are the many opportunities for errors associated with this prior technique. The conditioned gas line of the measurement instrument of the present invention allows for quick, easy in-stack equilibration both before and after sampling. The use of an inertial mass measurement transducer permits direct on-line near real-time mass measurement of collected particulate. The mass readings are directly available at the site, eliminating the need to transport the sample to a lab for postconditioning and weighing. Since it resolves mass in near real-time, the present instrument provides useful plant process information such as transient particulate mass concentrations during ramped loadings, stratification in stacks and control device efficiencies. It also facilitates the calibration of existing indirect continuous emission monitors. Finally, any particulate matter collected on the inlet tube wall during sampling can be subsequently loosened, collected and immediately weighed by the same instrument, resulting in an EPA Method 17 equivalent test. The operation of the instrument of the present invention reduces testing errors and provides an accurate and repeatable test protocol. The in-situ equilibrator and other teachings of the present invention can also advantageously be employed in mass measurement devices used in applications beyond stack monitoring.

Although presently preferred embodiments of the invention have been described and depicted herein, those skilled in the art will recognize that various modifications, substitutions and additions can be made without departing from the principles of this invention.

What is claimed is:

1. Apparatus for directly measuring mass of particulate of effluent gas flowing in a stack, comprising:

an inertial mass measurement assembly including a mass transducer, a particulate collector connected to said mass transducer, and an inlet tube for directing sampled gas towards said collector;

a support structure for supporting said mass measurement assembly within said stack with said inlet tube oriented for sampling effluent gas flowing in said stack whereby sampled effluent gas enters said tube and is directed toward said collector; and a conditioned gas supply line for selectively supplying conditioned gas to said transducer connected collector while said mass measurement assembly is supported and operational within said stack.

2. The apparatus of claim 1 further including a temperature controller associated with said supply line for controlling temperature of said conditioned gas.

3. The apparatus of claim 2 wherein said temperature controller comprises a heat exchanger for maintaining said conditioned gas at substantially the same temperature as said sampled effluent gas.

4. The apparatus of claim 3 wherein at least a section of said supply line upstream of said heat exchanger is heated.

5. The apparatus of claim 2 wherein said temperature controller in association with said supply line supplies said conditioned gas to said collector at a set temperature.

6. The apparatus of claim 1 wherein said conditioned gas comprises a desiccated clean gas.

7. The apparatus of claim 6 wherein said desiccated clean gas has a temperature when supplied to said collector substantially equal to a temperature of said sampled effluent gas.

8. The apparatus of claim 1 wherein said conditioned gas prevents effluent gas from reaching said collector.

9. The apparatus of claim 8 wherein said conditioned gas is introduced into said inlet tube at a flow rate which exceeds a flow rate of said sampled effluent gas.

10. The apparatus of claim 1 wherein said conditioned gas dilutes said sampled effluent gas.

11. The apparatus of claim 1 wherein said supply line includes a pump, a flow controller, a gas drier and a switching valve.

12. The apparatus of claim 11 wherein said supply line further includes a heat exchanger in said stack to bring the conditioned gas to a temperature of said sampled effluent gas.

13. The apparatus of claim 1 further including a controller mandating supply of said conditioned gas to said collector prior to a sampling period to precondition said collector and after said sampling period to post condition said collector and collected particulate.

14. The apparatus of claim 1 further including a controller mandating intermittent sampling of said effluent gas by said mass measurement assembly and mandating supply of said conditioned gas to said collector between sampling periods.

15. The apparatus of claim 1 wherein the effluent gas is sampled isokinetically and said inertial mass measurement instrument provide mass readings in near real time.

16. The apparatus of claim 1 wherein said mass transducer comprises a hollow elastic element vibrating in a clamp-free mode, and said collector comprises a filter mounted on a free end of said elastic element.

17. The apparatus of claim 1 further including an indicator connected to said mass transducer for indicating at least one of total mass and mass concentration of collected particulate with uncombined water substantially reduced.

18. The apparatus of claim 1 wherein said support structure includes an extendible boom inserted into said stack and supporting said mass measurement assembly at a remote end thereof.

19. The apparatus of claim 18 wherein said mass measurement assembly is pivotally mounted to said boom such that the assembly can be pivoted between a first orientation generally coaxial with the boom and a second orientation generally coaxial with the stack.

20. The apparatus of claim 19 further including a boom mounting arrangement which allows said mass measurement assembly to traverse said stack to sample said effluent gas at different locations within said stack.

21. The apparatus of claim 1 further including a sampling line for conveying gas from a vicinity of said collector to outside said stack, said sampling line including a condenser.

22. The apparatus of claim 21 wherein said sampling line further includes a heated section upstream of said condenser and a reduced pressure pump downstream of said condenser.

23. In an in-stack mass determining device which determines mass of material in an effluent gas flowing in a stack, the improvement comprising:
an inertial mass measurement transducer located within said stack and connected to a material collector for sampling said effluent gas and measuring mass of material collected from sampled effluent gas by said collector directly and in near real time, and an in-stack equilibrator for equilibrating the collector in the stack.

24. The improved mass determining device of claim 23 wherein said equilibrating comprises equilibrating the collector in the stack prior to sampling, and equilibrating the collector and the collected material in the stack after sampling.

25. The improved mass determining device of claim 24 wherein said in-stack equilibrator comprises a supply line for selectively supplying conditioned gas to said collector within said stack.

26. The improved mass determining device of claim 25 wherein said conditioned gas comprises desiccated, clean gas with a temperature substantially equal to a temperature of the sampled effluent gas.

27. A mass measurement system wherein material from an effluent gas flowing in a stack is collected on a collector within said stack for mass measurement purposes, and further comprising:
an in-situ equilibrator for equilibrating the collector within said stack.

28. The mass measurement system of claim 27 wherein said in-situ equilibrator comprises a supply line for selectively supplying conditioned gas to said collector within said stack to equilibrate the collector in situ.

29. The mass measurement system of claim 28 wherein said conditioned gas comprises desiccated, clean gas supplied at a set temperature and in a manner which prevents effluent gas from reaching said collector.

30. An inertial mass measurement device wherein a gas to be sampled is directed to flow along a sampling flow path and material from the gas is collected on a collector located along said flow path and connected to an inertial mass transducer for measurement purposes and further comprising:
an in-situ equilibrator for equilibrating the transducer connected collector within the device, said equilibrator selectively supplying conditioned gas to said collector alone the flow path in the same direction as the gas to be sampled flows.

31. The mass measurement device of claim 30 wherein the in-situ equilibrator equilibrates the collector within the device to provide a preconditioned collector for sampling.

32. The mass measurement device of claim 30 wherein the in-situ equilibrator equilibrates the collector and collected material on the collector within the device.

33. A method for measuring mass of material in an effluent gas flowing in a stack, comprising:
locating a material collector within said stack;
equilibrating the collector within the stack to provide a preconditioned collector;
sampling the effluent gas flowing in the stack;
collecting material from sampled effluent gas on the preconditioned collector within the stack;
equilibrating the collector and collected material within the stack to provide a post conditioned collector and collected material; and measuring a mass change of said post conditioned collector and collected material relative to said preconditioned collector.

34. The method of claim 33 wherein said equilibrating comprises directing dry clean heated gas towards said collector, and said measuring comprises determining said mass increase with an inertial mass measurement transducer connected to said collector and located in the stack.

35. The method of claim 34 further including:

directing the sampled effluent gas to the preconditioned collector with an inlet tube;

after sampling, brushing down an interior of the inlet tube to collect any additional material which may have lodged on said interior during sampling; and measuring mass of said additional material with said inertial mass measurement instrument.

* * * * *

UNITED STATES PATENT AND TRADEMARK OFFICE
CERTIFICATE OF CORRECTION

PATENT NO. : 5,970,781
DATED : October 26, 1999
INVENTOR(S) : Hiss, III et al.

It is certified that error appears in the above-identified patent and that said Letters Patent is hereby corrected as shown below:

Col. 7, line 1, delete "$4\pi^2 f^2 = K/m$" and replace with -- $4\pi^2 f^2 = K/m$ --.

Col. 7, line 4, delete "$f^2 = K_0/m$" and replace with -- $f^2 = K_0/m$ --.

IN THE CLAIMS:

Claim 30, Col. 12, line 49, delete "alone" and replace with --along--.

Signed and Sealed this

Sixteenth Day of May, 2000

Attest:

Q. TODD DICKINSON

*Attesting Officer*     *Director of Patents and Trademarks*